US008245652B2

(12) United States Patent
Hung (10) Patent No.: US 8,245,652 B2
(45) Date of Patent: Aug. 21, 2012

(54) MEDICAL WORKTABLE

(75) Inventor: Chin-Jui Hung, Wu-Chi Chen (TW)

(73) Assignee: Modernsolid Industrial Co., Ltd., Wu-Chi Chen, Taichung Hsien (TW)

( * ) Notice: Subject to any disclaimer, the term of this patent is extended or adjusted under 35 U.S.C. 154(b) by 341 days.

(21) Appl. No.: 12/661,847

(22) Filed: Mar. 25, 2010

(65) Prior Publication Data

US 2011/0232535 A1  Sep. 29, 2011

(51) Int. Cl.
*A47B 37/00* (2006.01)
(52) U.S. Cl. .................. 108/50.02; 108/147; 248/188.5; 280/47.35
(58) Field of Classification Search ............... 312/223.3; 108/147, 25, 50.02, 20; 280/47.34, 47.35, 280/79.11; 297/344.19; 248/162.1, 157, 248/631, 188.2, 188.5
See application file for complete search history.

(56) References Cited

U.S. PATENT DOCUMENTS

| | | | | |
|---|---|---|---|---|
| 684,842 | A * | 10/1901 | Merker | 60/436 |
| 2,636,348 | A * | 4/1953 | Murray | 60/467 |
| 3,285,207 | A * | 11/1966 | Vom Hagen | 108/146 |
| 4,183,689 | A * | 1/1980 | Wirges et al. | 403/31 |
| 4,485,996 | A * | 12/1984 | Beukema et al. | 248/407 |
| 4,673,155 | A * | 6/1987 | Binder | 248/404 |
| 5,765,804 | A * | 6/1998 | Stumpf et al. | 248/631 |
| 6,378,816 | B1 * | 4/2002 | Pfister | 248/161 |
| 7,009,840 | B2 * | 3/2006 | Clark et al. | 361/679.41 |
| 7,306,192 | B2 * | 12/2007 | Sopp | 248/404 |
| 7,594,668 | B2 * | 9/2009 | Arceta et al. | 280/47.35 |
| 7,621,544 | B2 * | 11/2009 | Rossini | 280/79.3 |
| 7,673,941 | B2 * | 3/2010 | King et al. | 297/344.19 |
| 8,091,841 | B2 * | 1/2012 | Jones et al. | 248/125.2 |
| 2005/0022661 | A1 * | 2/2005 | Zanden | 91/437 |
| 2007/0228680 | A1 * | 10/2007 | Reppert et al. | 280/47.35 |
| 2009/0015051 | A1 * | 1/2009 | Haeberle | 297/344.19 |
| 2011/0042911 | A1 * | 2/2011 | Kozlowski et al. | 280/47.35 |
| 2011/0272902 | A1 * | 11/2011 | Arceta et al. | 280/47.35 |

* cited by examiner

*Primary Examiner* — Janet M Wilkens
(74) *Attorney, Agent, or Firm* — Charles E. Baxley (57) ABSTRACT

A medical worktable has a base, a lifting device and a platform device. The base has a lower casing and an upper casing detachably connected to the lower casing. The lifting device is adjustably mounted on the base and has a pressurized air cylinder, an inner tube and an outer tube. The pressurized air cylinder is mounted in the upper casing and is securely mounted on the lower casing. The inner tube is mounted around the pressurized air cylinder and abuts the cylinder shaft. The outer tube is mounted around the inner tube and is securely mounted on a mounting board of the pressurized air cylinder. The platform device is mounted on the lifting device, is opposite to the base and has a mounting seat and a platform. The mounting seat is securely connected to the inner tube. The platform is mounted on a top of the mounting seat.

10 Claims, 7 Drawing Sheets

MEDICAL WORKTABLE

BACKGROUND OF THE INVENTION

1. Field of the Invention

The present invention relates to a medical worktable, and more particularly to a medical worktable that can be operated conveniently to provide preferably enquiry.

2. Description of Related Art

When a physician enquires about an inpatients' condition, a conventional medical worktable is used to carry case notes, medicines, articles and instruments for medical use to immediately record patient state and provide simple nursing. A conventional medical worktable has a base, a stand and a platform. The base has multiple wheels aid portability. The stand is securely mounted on and protrudes from the base and has an upper end. The platform is mounted on the upper end of the stand.

Although the conventional medical worktable can provide carrying and transporting effects, height of the platform is unchangeable and the height of the platform can not be adjusted according to different needs. In addition, the conventional worktable does not have a power supply and can not be electrically connected to a computer, a display or other medical instruments, so medical personnel are limited in treatments that may be provided based on the medical worktable and with digitization of many medical records, portable computers are frequently used to record notes and write prescriptions for central processing.

Therefore, the present invention provides a medical worktable that mitigates or obviates the aforementioned problems.

SUMMARY OF THE INVENTION

The main objective of the invention is to provide a medical worktable that can be operated conveniently to provide preferably enquiry.

The medical worktable in accordance with the present invention has a base, a lifting device and a platform device. The base has a lower casing and an upper casing detachably connected to the lower casing. The lifting device is adjustably mounted on the base and has a pressurized air cylinder, an inner tube and an outer tube. The pressurized air cylinder is mounted in the upper casing and is securely mounted on the lower casing. The inner tube is mounted around the pressurized air cylinder and abuts a top end of the cylinder shaft. The outer tube is mounted around the inner tube and is securely mounted on a mounting board of the pressurized air cylinder. The platform device is mounted on the lifting device, is opposite to the base and has a mounting seat and a platform. The mounting seat is securely connected to the inner tube. The platform is mounted on a top of the mounting seat.

Other objects, advantages and novel features of the invention will become more apparent from the following detailed description when taken in conjunction with the accompanying drawings.

DETAILED DESCRIPTION OF PREFERRED EMBODIMENT

With reference to FIGS. 1 to 6, a medical worktable in accordance with the present invention comprises a base (10), a lifting device (20) and a platform device (30).

The base (10) has a lower casing (11), an upper casing (12) and a transformer (16).

The lower casing (11) has a front side, a rear side, a sidewall, a chamber, a top face, multiple wheels (111), multiple brakes (112), multiple elongated holes (113), a battery (13) and a radiator (14). The wheels (111) are rotatably mounted on the lower casing (11). The brakes (112) are connected to some of the wheels (111) to provide a braking effect to the wheels (111). The elongated holes (113) are formed through the sidewall of the lower casing (11) near the rear side. The battery (13) is mounted in the chamber of the lower casing (11) near the front side. The radiator (14) is mounted in the chamber of the lower casing (11) near the elongated holes (113) to eliminate heat of the lower casing (11) via the elongated holes (113) and is electrically connected to the battery (13).

The upper casing (12) is detachably connected to the lower casing (11) and has an outlet (15). The outlet (15) is mounted in the upper casing (12) and is electrically connected to the battery (13) to provide a charging effect for the battery (13).

The transformer (16) is mounted in the base (10) and is electrically connected to the battery (13) of the lower casing (11) and the outlet (15) of the upper casing (12) to transfer the direct current provided by the battery (13) to the alternating current applied to the outlet (15).

The lifting device (20) is adjustably mounted on the base (10) and has a pressurized air cylinder (21), an inner tube (22), an outer tube (23) and a decorative casing (24).

The pressurized air cylinder (21) is mounted in the upper casing (12), is securely mounted on the lower casing (11) and has a lower end, an upper end, a mounting board (211) and a cylinder shaft (25). The upper end of the pressurized air cylinder (21) extends out of the upper casing (12) of the base (10). The mounting board (211) is mounted on the lower end of the pressurized air cylinder (21) and is securely mounted on the top face of the lower casing (11). The cylinder shaft (25) is movably mounted in the pressurized air cylinder (21), extends out of the upper end of the pressurized air cylinder (21) and has a top end, a pneumatic switch (251), a mounting jacket (252) and an oil pressure valve (253). The pneumatic switch (251) is pressably mounted on the top end of the cylinder shaft (25). The mounting jacket (252) is mounted around the top end of the cylinder shaft (25). The oil pressure valve (253) is mounted in the mounting jacket (252) and may contact with the pneumatic switch (251).

The inner tube (22) is mounted around the pressurized air cylinder (21), abuts the top end of the cylinder shaft (25) and has a top end, an external surface, an internal surface, a linking board (221), a gap (222), a top board (223), at least one guiding groove (224), multiple balls (225) and a holding panel (226). The linking board (221) may be sectorial and is formed on and protrudes from the external surface of the inner tube (22) near the top end. The gap (222) is formed through the external surface of the inner tube (22) in the top end. The top board (223) is formed on the internal surface of the inner tube (22) and abuts the mounting jacket (252) of the cylinder shaft (25). The at least one groove (224) is formed on the external surface of the inner tube (22) and is parallel with the cylinder shaft (25). The balls (225) are movably mounted in the at least one groove (224). The holding panel (226) is mounted on the external surface of the inner tube (22) to hold the balls (225) in the at least one groove (224).

The outer tube (23) is mounted around the inner tube (22), is securely mounted on the mounting board (211) of the pressurized air cylinder (21) and abuts the balls (225) of the inner tube (22). When the cylinder shaft (25) pushes the mounting jacket (252) against the top board (223), the inner tube (22) will move upward relative to the outer tube (23).

The decorative casing (24) is mounted around the outer tube (23), is securely mounted on the mounting board (211) of the pressurized air cylinder (21) and has a mounting tube (241) mounted around the outer tube (23).

The platform device (30) is mounted on the lifting device (20), is opposite to the base (10) and has a mounting seat (31) and a platform (32).

The mounting seat (31) is securely connected to the inner tube (22) of the lifting device (20) and has a bottom, a top, a rear side, a front side, two sidewalls, two rails (311), a pulling board (33), a store box (34) and an extending board (35). The bottom of the mounting seat (31) is securely mounted on the linking board (221) of the inner tube (22). The rails (311) are respectively mounted in the mounting seat (31) near the sidewalls and are parallel to each other. The pulling board (33) is connected to the rails (311) and can be moved out of the rear side of the mounting seat (31) along the rails (311). The store box (34) is mounted on the front side of the mounting seat (31) above the upper casing (12) to store case notes of inpatients or the like. The extending board (35) is mounted on one of the sidewalls of the mounting seat (31) near the store box (34) to hold cups or other medical objects.

The platform (32) is mounted on the top of the mounting seat (31) and has a front side, a rear side, a sidewall, a top face, a covering panel (321), a controlling button (36), an electric quantity display (37), a supporting rod (38) and two gripping holes (39). Preferably, the platform (32) is pivotally connected to the sidewalls of the mounting seat (31) near the front side. The covering panel (321) is detachably mounted on the top of the mounting seat (31) near the front side of the mounting seat (31).

The controlling button (36) is electrically connected to the cylinder shaft (25) of the lifting cylinder (20), is connected to an oil tank and has an oil pipe (361) and a protective cap (362). The oil pipe (361) extends through the gap (222) of the inner tube (22), communicates with the oil tank and is connected to the oil pressure valve (253) in the mounting jacket (252) to transport oil into or out of the oil pressure valve (253) from the oil tank. The protective cap (362) is mounted around the controlling button (36) and is securely mounted on the sidewall of the platform (32) to prevent accidental activation of the controlling button (36).

The electric quantity display (37) is mounted on the top face of the platform (32) near the rear side and is electrically connected to the transformer (16) of the base (10) to display battery life of the battery (13). The supporting rod (38) is mounted in the platform (32) near the front side and extends out of the covering panel (321) to hold a monitor or a display. The gripping holes (39) are formed through the top face of the platform (32) near the rear side to allow the user pushing the medical worktable by holding the griping holes (39) of the platform (32).

Figure 1:
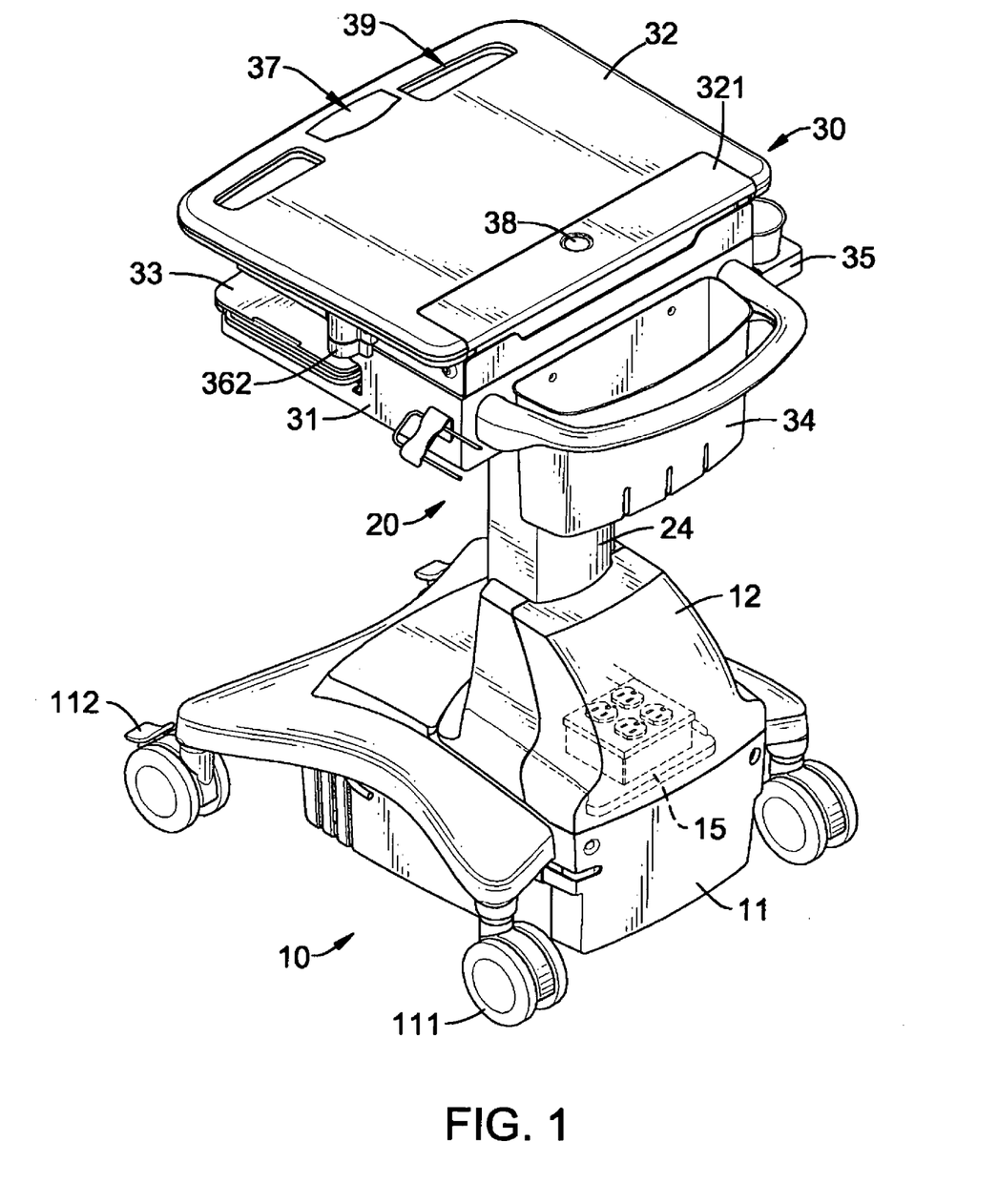
FIG. 1 is a perspective view of a medical worktable in accordance with the present invention.
Figure 2:
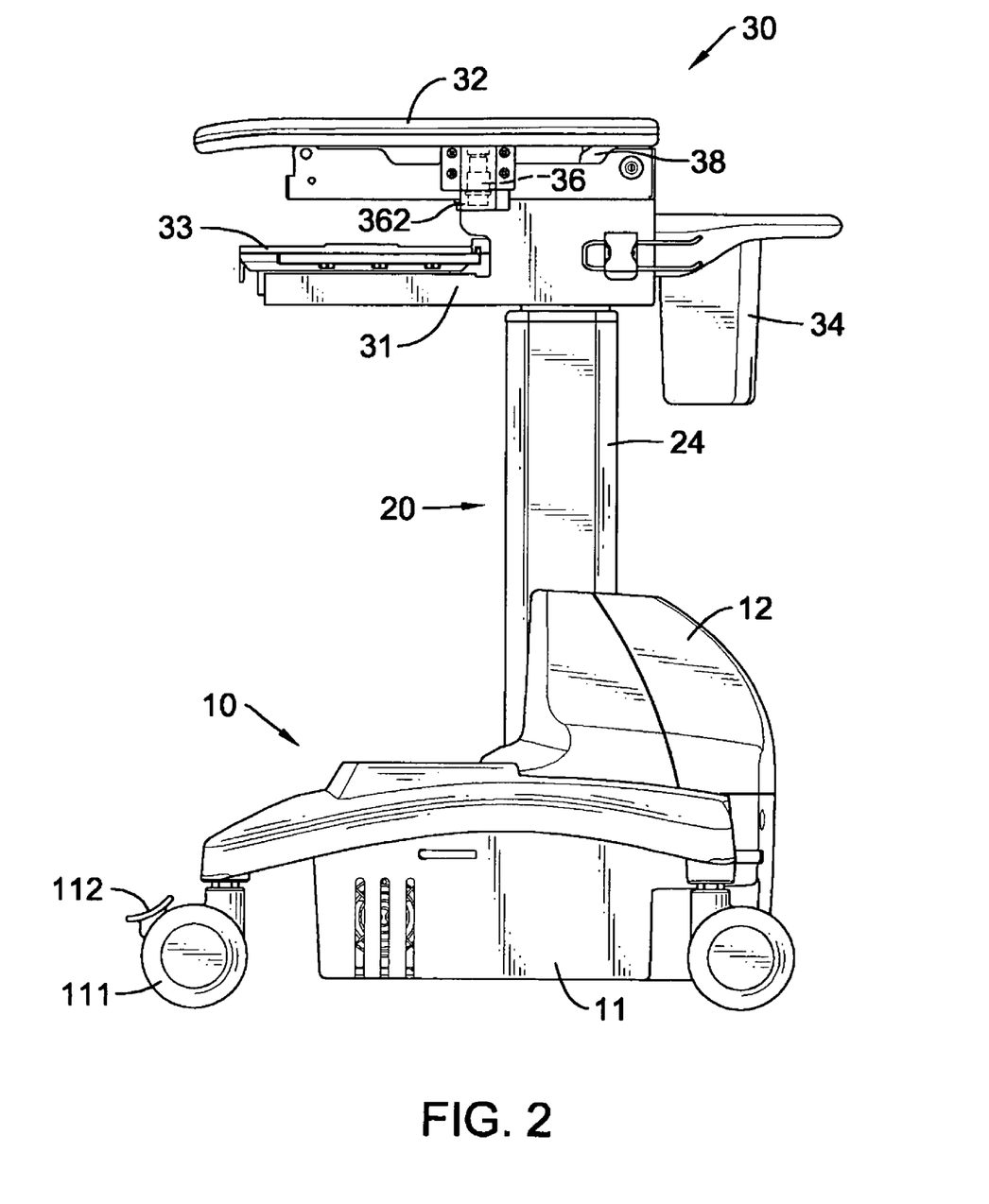
FIG. 2 is a side view of the medical worktable in FIG. 1.
Figure 3:
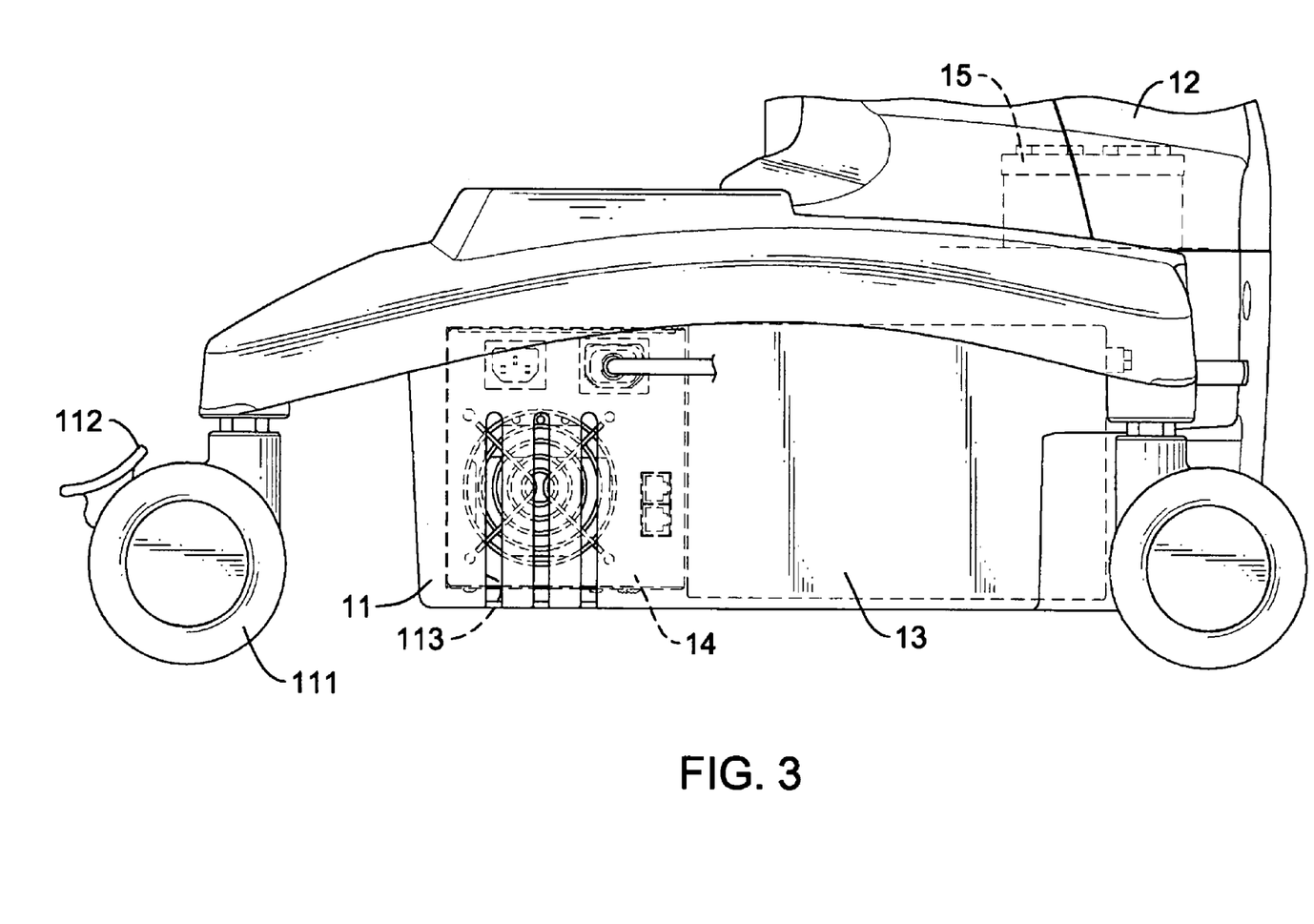
FIG. 3 is an enlarged side view of the medical worktable in FIG. 1.
Figure 4:
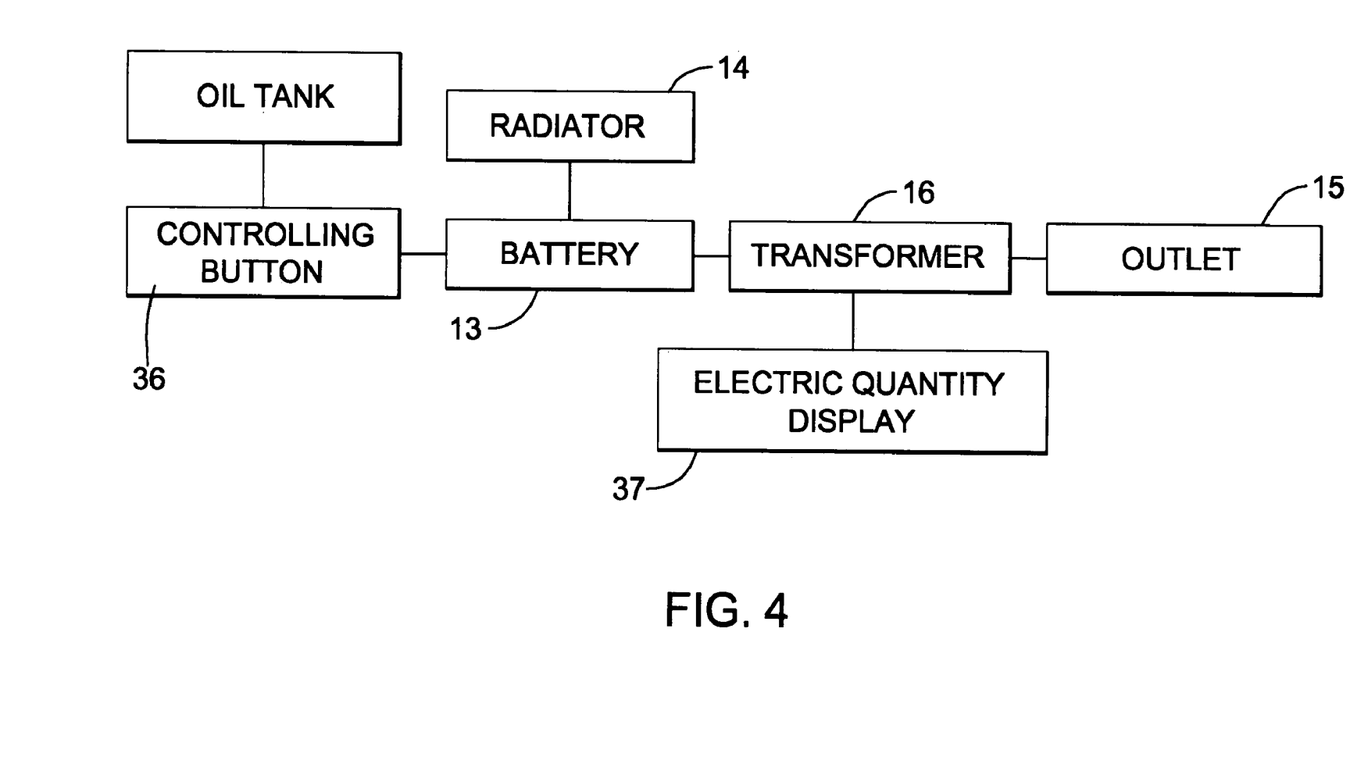
FIG. 4 is a block diagram of the medical worktable in accordance with the present invention.
Figures 5A, 5B:
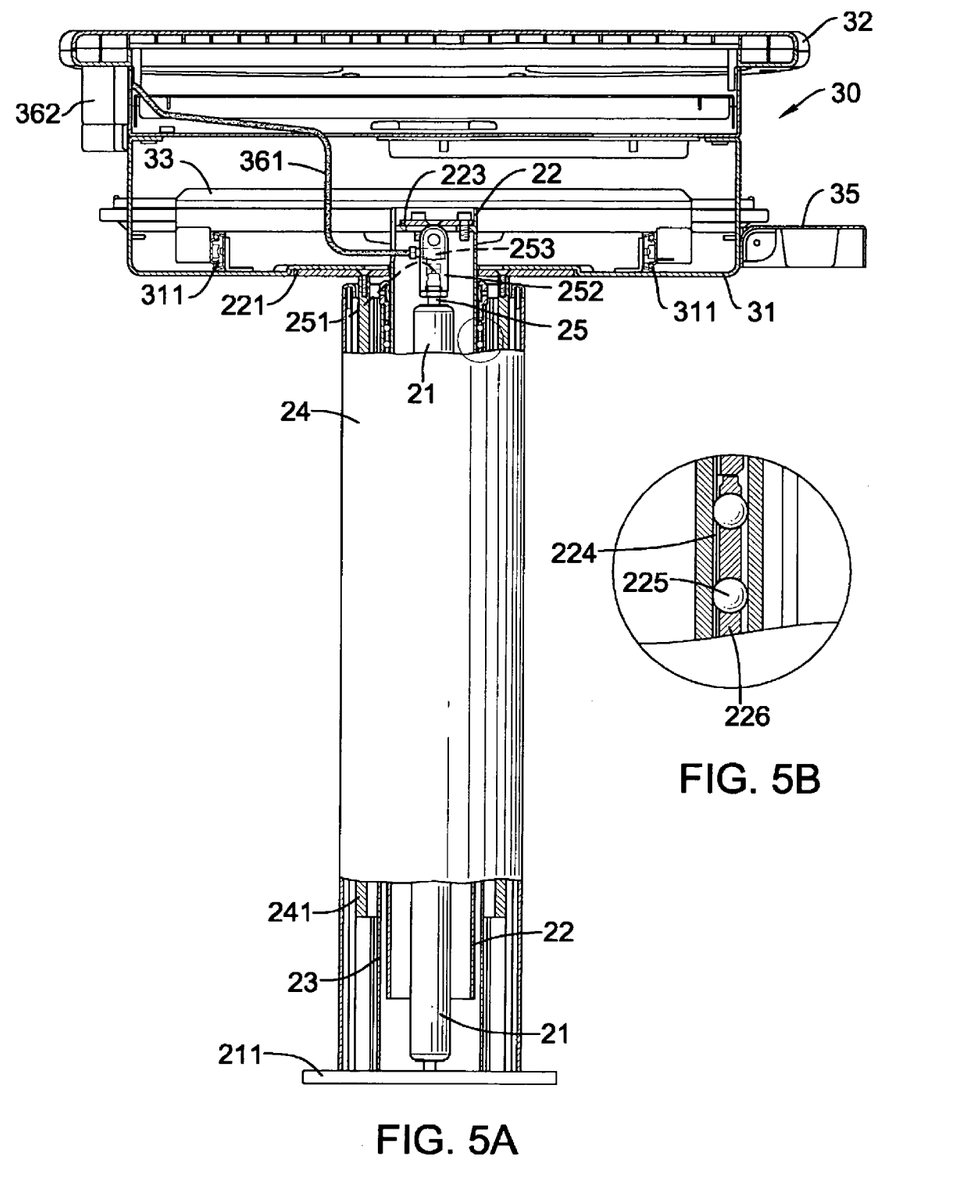
FIG. 5A is another enlarged side view in partial section of the medical worktable in FIG. 1.
FIG. 5B is enlarged side view of the medical worktable in FIG. 5A.
Figure 6:
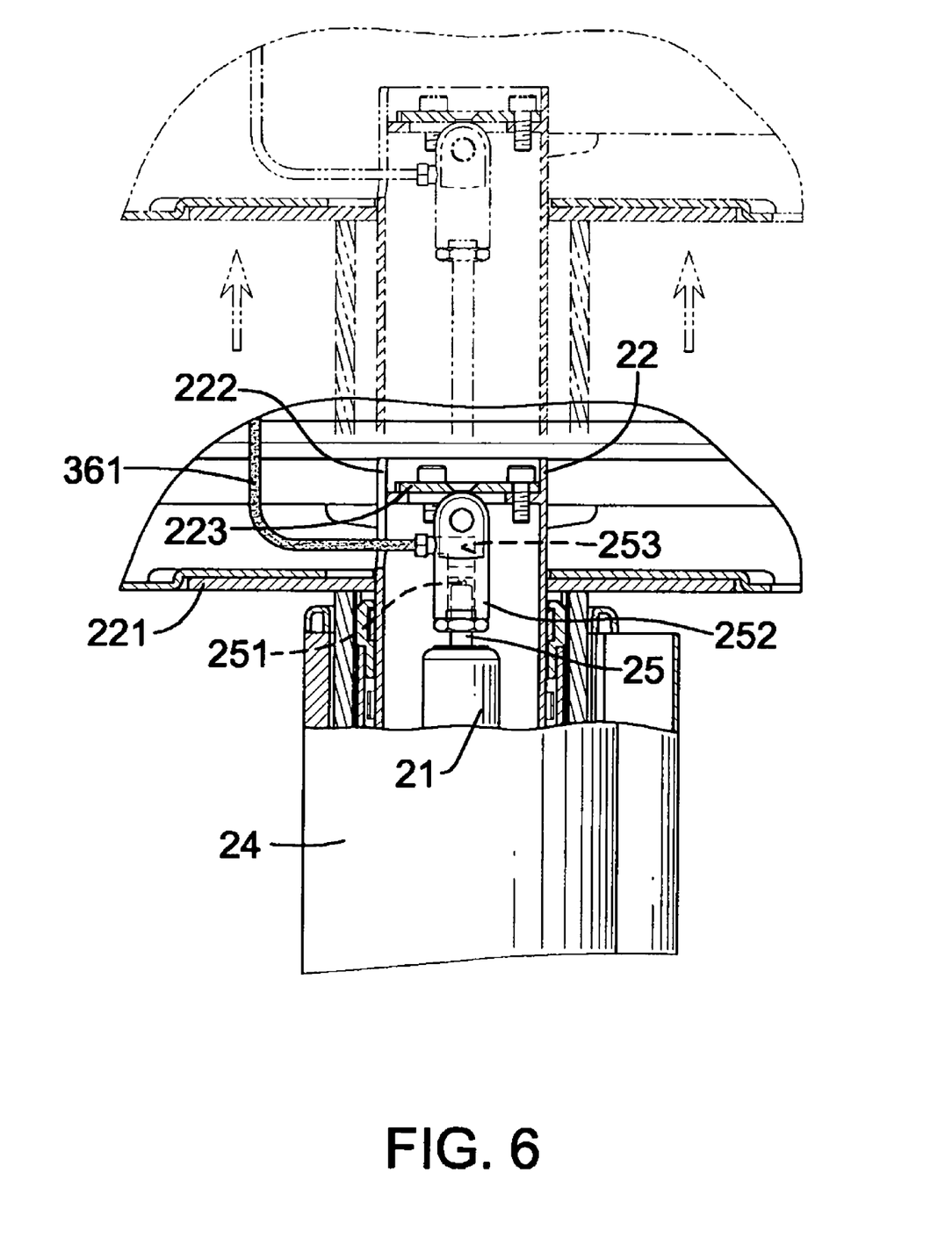
FIG. 6 is an operational side view in partial section of the medical worktable in FIG. 1.

When height of the medical worktable in accordance with the present invention requires adjustment, with reference to FIGS. 5 and 6, the oil stored in the oil tank can be led into the oil pressure valve (253) via the oil pipe (361) by pressing the controlling button (36). Then, the oil pressure valve (253) will abut and start the pneumatic switch (251) to allow the cylinder shaft (25) to move upward relative to the pressurized air cylinder (21). When the cylinder shaft (25) moves upward relative to the pressurized air cylinder (21), the inner tube (22) can be moved with the cylinder shaft (25) relative to the outer tube (23) by the mounting jacket (252) pressing against the top board (223) of the inner tube (22). Therefore, the mounting seat (31) that is securely mounted on the linking board (221) will move with the inner tube (23) so will move upward relative to the base (10) to increase the height of the medical worktable. In addition, to lower the height of the platform (32), the controlling button (36) is pressed and the platform (32) is pushed downward by the user to retract the cylinder shaft (25) into the pressurized air cylinder (21). Then, the height of the medical worktable can be adjusted by moving position of the inner tube (22) relative to the outer tube (23).

Furthermore, the medical worktable in accordance with the present invention can supply electric power to a computer, a display or other medical instruments by the battery (13) and the outlet (15) and can show battery life on the electric quantity display (37). Therefore, further treatments or analysis can be performed to provide a preferably enquiry for inpatients. In addition, the extending board (35) and the store box (34) can be used to hold or store case notes of the inpatients, medicines and the articles and instruments for medical use.

Figure 7:
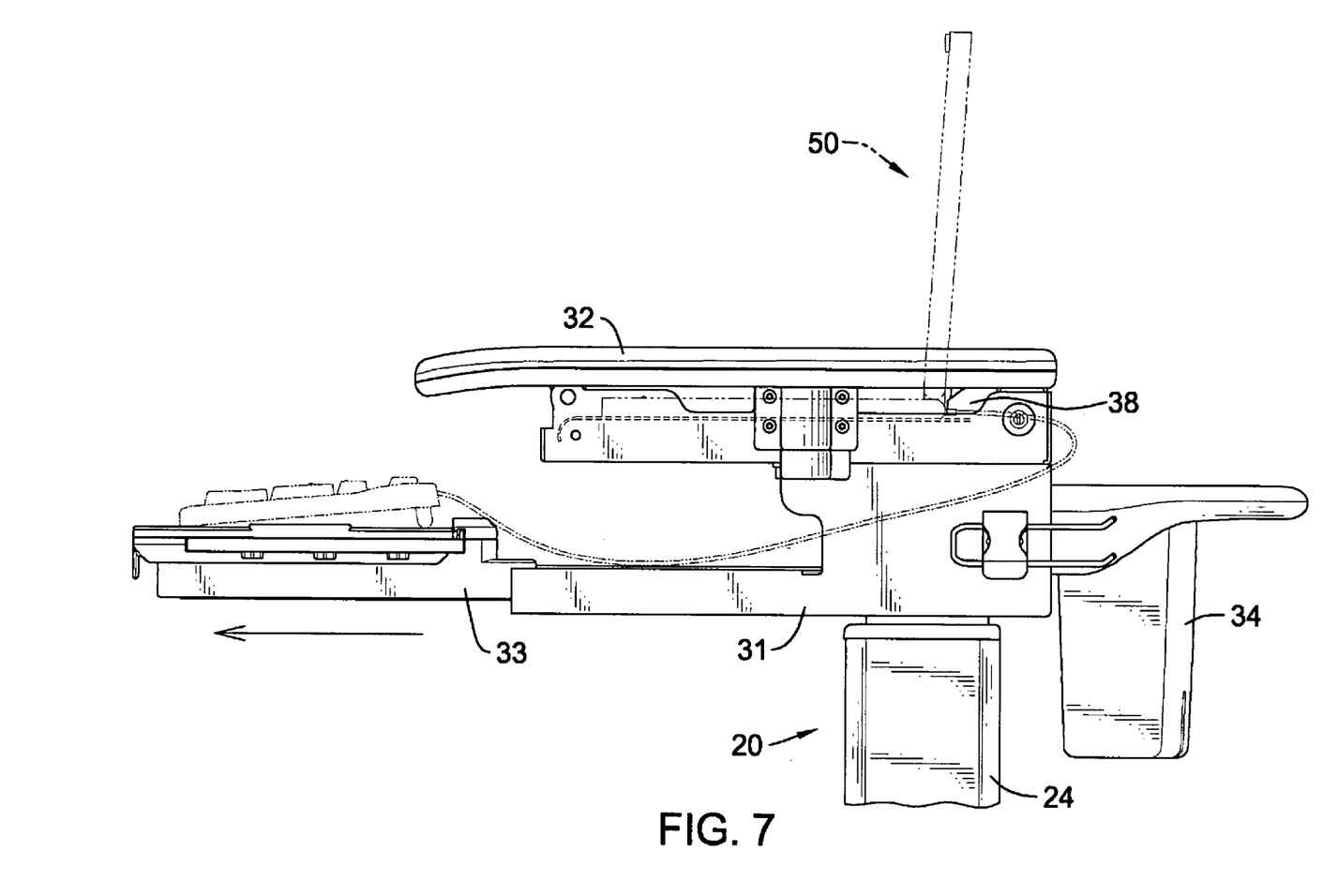
FIG. 7 is another operational side view of the medical worktable in FIG. 1.

With further reference to FIG. 7, in use, a notebook (50) can be placed in the platform (32) and the display of the notebook (50) can be extended out of the platform (32) from the covering panel (321). In addition, a mouse or a keyboard can be placed on the pulling panel (33) of the mounting seat (31) and is electrically connected to the notebook (50). Then, the pulling panel (33) can be extended relative to the mounting seat (31) to operate the mouse or the keyboard on the pulling panel (33). Furthermore, the battery (13) can supply electric power to the notebook (50), and the physician can immediately record the inpatients' conditions in the notebook (50) and provide an instant treatment to the inpatients accordingly.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:
1. A medical worktable comprising:
  a base having
    a lower casing having
      a front side;
      a rear side;
      a sidewall;
      a chamber;
      a top face; and
      multiple wheels rotatably mounted on the lower casing; and an upper casing detachably connected to the lower casing;
a lifting device adjustably mounted on the base and having
a pressurized air cylinder mounted in the upper casing, securely mounted on the lower casing and having
a lower end;
an upper end extending out of the upper casing of the base;
a mounting board mounted on the lower end of the pressurized air cylinder and securely mounted on the top face of the lower casing; and
a cylinder shaft movably mounted in the pressurized air cylinder, extending out of the upper end of the pressurized air cylinder and having a top end;
an inner tube mounted around the pressurized air cylinder, abutting the top end of the cylinder shaft and having
a top end;
an external surface;
an internal surface;
a linking board formed on and protruding from the external surface of the inner tube near the top end of the inner tube;
at least one guiding groove formed on the external surface of the inner tube and being parallel with the cylinder shaft;
multiple balls movably mounted in the at least one groove; and
a holding panel mounted on the external surface of the inner tube to hold the balls in the at least one groove; and
an outer tube mounted around the inner tube, securely mounted on the mounting board of the pressurized air cylinder and abutting the balls of the inner tube; and
a platform device mounted on the lifting device opposite to the base and having
a mounting seat securely connected to the inner tube of the lifting device and having
a bottom securely mounted on the linking board of the inner tube;
a top;
a rear side;
a front side;
two sidewalls; and
a platform mounted on the top of the mounting seat and having
a front side;
a rear side;
a sidewall;
a top face; and
a controlling button connected to the cylinder shaft of the pressurized air cylinder and connected to an oil tank.

2. The medical worktable as claimed in claim 1, wherein
the lower casing has a battery mounted in the chamber of the lower casing near the front side;
the upper casing has an outlet mounted in the upper casing and electrically connected to the battery to provide a charging effect for the battery;
the base has a transformer mounted in the base and electrically connected to the battery of the lower casing and the outlet of the upper casing to transfer the electric current; and
the platform has an electric quantity display mounted on the top face of the platform near the rear side and electrically connected to the transformer of the base to show the electric quantity of the battery.

3. The medical worktable as claimed in claim 2, wherein
the platform is pivotally connected to the sidewalls of the mounting seat near the front side and has a covering panel detachably mounted on the top of the mounting seat near the front side of the mounting seat;
the cylinder shaft has
a pneumatic switch pressably mounted on the top end of the cylinder shaft;
a mounting jacket mounted around the top end of the cylinder shaft; and
an oil pressure valve mounted in the mounting jacket to contact with the pneumatic switch;
the inner tube has
a gap formed through the external surface of the inner tube in the top end; and
a top board formed on the internal surface of the inner tube and abutting the mounting jacket of the cylinder shaft; and
the controlling button has an oil pipe extended through the gap of the inner tube, communicating with the oil tank and connected to the oil pressure valve in the mounting jacket to transport oil into or out of the oil pressure valve from the oil tank.

4. The medical worktable as claimed in claim 3, wherein the platform has
a supporting rod mounted in the platform near the front side and extending out of the covering panel to hold a display; and
two gripping holes formed through the top face of the platform near the rear side to allow the user pushing the medical worktable by holding the griping holes of the platform.

5. The medical worktable as claimed in claim 4, wherein
the lifting device has a decorative casing mounted around the outer tube, securely mounted on the mounting board of the pressurized air cylinder and having a mounting tube mounted around the outer tube; and
the controlling button has a protective cap mounted around the controlling button and securely mounted on the sidewall of the platform to prevent from mis-pressing the controlling button.

6. The medical worktable as claimed in claim 5, wherein the mounting seat has
two rails respectively mounted in the mounting seat near the sidewalls and parallel to each other;
a pulling board connected to the rails and can be moved out of the rear side of the mounting seat along the rails;
a store box mounted on the front side of the mounting seat above the upper casing to store case notes of inpatients or the like; and
an extending board mounted on one of the sidewalls of the mounting seat near the store box to hold cups or other medical objects.

7. The medical worktable as claimed in claim 6, wherein the lower casing has
multiple elongated holes formed through the sidewall of the lower casing near the rear side; and
a radiator mounted in the chamber of the lower casing near the elongated holes to eliminate heat of the lower casing via the elongated holes and electrically connected to the battery.

8. The medical worktable as claimed in claim 7, wherein the lower casing has multiple brakes connected the wheels to provide a braking effect to the wheels.

9. The medical worktable as claimed in claim 1, wherein
the lifting device has a decorative casing mounted around the outer tube, securely mounted on the mounting board of the pressurized air cylinder and having a mounting tube mounted around the outer tube; and the controlling button has a protective cap mounted around the controlling button and securely mounted on the sidewall of the platform to prevent accidental activation of the controlling button.

10. The medical worktable as claimed in claim 1, wherein the mounting seat has two rails respectively mounted in the mounting seat near the sidewalls and parallel to each other;

a pulling board connected to the rails and can be moved out of the rear side of the mounting seat along the rails;

a store box mounted on the front side of the mounting seat above the upper casing to store case notes of inpatients or the like; and an extending board mounted on one of the sidewalls of the mounting seat near the store box to hold cups or other medical objects.

* * * * *